US006282440B1

(12) United States Patent
Brodnick et al.

(10) Patent No.: US 6,282,440 B1
(45) Date of Patent: Aug. 28, 2001

(54) METHOD TO IDENTIFY ELECTRODE PLACEMENT

(75) Inventors: Donald E. Brodnick, Cedarburg; Paul P. Elko, River Hills, both of WI (US)

(73) Assignee: GE Marquette Medical Systems, Inc., Milwaukee, WI (US)

( * ) Notice: Subject to any disclaimer, the term of this patent is extended or adjusted under 35 U.S.C. 154(b) by 0 days.

(21) Appl. No.: 09/477,782

(22) Filed: Dec. 31, 1999

(51) Int. Cl.$^7$ .................................................. A61B 5/0452

(52) U.S. Cl. ............................................................ 600/512

(58) Field of Search ..................................... 600/509, 512

(56) References Cited

U.S. PATENT DOCUMENTS 4,987,901 * 1/1991 Kunig .

OTHER PUBLICATIONS

Geselowitz, "Some Comments on the Status of Electrocardiographic Lead Systems," *Computer application on ECG and VCG analysis*, pp. 10–21 (1973).
M.E. Womble, et al., "Data Compression for Storing and Transmitting ECG's/VCG's," Proceedings of the IEEE, vol. 65, No. 5, pp. 702–706 (May 1977).
P.M. Rautaharju, et al., "The Effect of Modified Limb Electrode Positions on Electrocardiographic Wave Amplitudes," *J. Electrocardiology* 13(2), pp. 109–114 (1980).
P. Gamble, et al., "A Comparison of the Standard 12–Lead Electrocardiogram to Exercise Electrode Placements," *Chest*, vol. 85, pp. 616–622 (May, 1984).
N.E. Hill, et al., "Importance of Accurate Placement of Precordial Leads in the 12–Lead Electrocardiogram," *Heart & Lung*, vol. 16, No. 5, pp. 561–566 (Sep. 1987).

D. Sevilla, et al., "Invalidation of the Resting Electrocardiogram Obtained Via Exercise Electrode Sites as a Standard 12–Lead Recording," *The American Journal of Cardiology*, pp. 35–39 (Jan. 1, 1989).
M.V. Herman, et al., "Variability of Electrocardiographic Precordial Lead Placement: A Method to Improve Accuracy and Reliability," *Clin. Cardiol*, vol. 14, pp. 469–476 (Jun. 1991).
O. Pahlm, et al., "Evaluation of Changes in Standard Electrocardiographic QRS Waveforms Recorded from Activity–Compatible Proximal Limb Lead Positions," *The American Journal of Cardiology*, vol. 69, pp. 253–257 (Jan. 15, 1992).
J. Bartosik, et al., "Reconstruction of the Standard 12–Lead ECG From Recordings Using Nonstandard Activity–compatible Proximal Limb Lead Positions," *Journal of Electrocardiology*, vol. 28 No. 1, pp. 33–38 (Jan. 1995).

* cited by examiner

Primary Examiner—Scott M. Getzow
(74) Attorney, Agent, or Firm—Michael Best & Friedrich LLP (57) ABSTRACT

An ECG signal is acquired in multiple channels, and sources of interference are filtered from the signals. A covariance matrix is then formed with the channels of data. The invention then employs matrix mathematics to discover a set of eigenvectors that organize the variability of data in a multi-dimensional space along new directions, orthogonal to each other and ranked in order of significance. For each eigenvector, a corresponding eigenvalue is calculated. In addition, coefficients are calculated which correspond to the portion of each eigenvector that is necessary to reconstruct each original vector. From the eigenvector solution of the covariance matrix, the angles between the eigenvectors and the original vectors are determined. The eigenvector coefficients and the angles between the eigenvectors and the original vectors are related by a cosine relationship. The angles calculated for each particular ECG test are compared to a reference set of angles to determine whether the electrodes are placed in the standard ECG electrode placement, an alternative electrode placement, or an incorrect electrode placement.

30 Claims, 12 Drawing Sheets

| Eigenvalue |
|---|
| 351.634 |
| 28.566 |
| 3.300 |
| 0.791 |
| 0.199 |
| 0.075 |
| 0.039 |
| 0.026 |

| Eigenvector | e1 | e2 | e3 |
|---|---|---|---|
| I | -0.216 | 0.158 | 0.122 |
| II | -0.314 | -0.193 | -0.835 |
| V1 | 0.060 | -0.570 | -0.207 |
| V2 | -0.156 | -0.600 | 0.230 |
| V3 | -0.344 | -0.381 | 0.363 |
| V4 | -0.522 | 0.001 | 0.182 |
| V5 | -0.529 | 0.238 | 0.055 |
| V6 | -0.396 | 0.228 | -0.156 |

METHOD TO IDENTIFY ELECTRODE PLACEMENT

BACKGROUND OF THE INVENTION

The invention relates to measuring a physiological characteristic of a patient, and particularly, to an electrocardiograph including a method and apparatus for identifying the relative position of the electrodes connected to the patient.

It is commonly known that ten electrodes and ten leadwires are needed to record and present what is commonly referred to as a twelve lead electrocardiogram (ECG), i.e., a group of twelve signals representing twelve different "views" of the electrical activity in the patient's heart. For standard or resting ECG electrode placement, one electrode is attached to each of the four body limbs at the right wrist, left wrist, right ankle, and left ankle. Additionally, six electrodes are attached to the chest over the heart. The ten electrodes connect via several resistor networks to enough amplifiers to record twelve channels of ECG. The twelve leads (i.e., signals) are generally split into two groups comprising the frontal plane and the horizontal plane. The frontal plane leads (I, II, III, aVr, aVl, aVf) are variously referred to as limb leads, Einthoven leads, or bipolar leads. The horizontal plane leads (v1, v2, v3, v4, v5, v6) are likewise variously referred to as precordial leads, chest leads, or unipolar leads.

Accurate placement of the electrodes on the patient's body surface is required to record a useful ECG using an electrocardiograph or patient monitor. The ideal placement of electrodes for a standard ECG is well defined and accepted within the medical industry. However, routine correct placement of the electrodes in the clinical environment is difficult to achieve for several reasons. First, nurses and ECG technicians are frequently not adequately trained or are too inexperienced to accurately locate the attachment points. Moreover, individual physical characteristics vary widely from patient-to-patient. These variations lead to misinterpretation of the "anatomical guideposts" used to locate the proper attachment points. Additionally, patients sometimes have wounds or bandages that preclude access to the patient's body surface at the proper attachment points. Also, attachment of the electrodes to an ECG machine is often accomplished using long individual ECG leadwires. Even if the electrodes are accurately placed on the patient, the leadwires connecting them to the electrocardiograph may be crossed such that signals are switched at the instrument.

Many inventors have attempted to solve the problem of electrode connection to the chest. Numerous belts, pads, vests, harnesses and strip electrodes have been developed that place a multitude of electrodes into an ordered arrangement to facilitate the attachment of the leads to the patient and eliminate the possibility of some types of attachment errors. In general, these inventions attempt to fix the six horizontal electrodes in relation to each other while adapting to different patient sizes. None of these teachings address the issue of placement of the limb electrodes. Moreover, the location of the horizontal lead electrodes may still not be at the proper anatomical positions.

In some ECG applications the patient must be free to move. Thus, it becomes inconvenient or impossible to place the electrodes on the wrists and ankles. Applications where the patient must be free to move include long term recordings, known as holter; ambulatory patient monitoring, such as telemetry monitoring; and exercise testing on treadmills or bicycles, known as stress testing. In these tests, the wrist and ankle electrode positions are unacceptable for electrode placement due to inconvenience, increased danger of tangling of the lead wires, and increased noise from limbs in motion. Generally, in each of these ECG applications the limb electrodes are moved onto the torso and placed near the shoulders and hips. The Mason-Likar system is one variation of electrode placement on the torso. Twelve-lead bedside monitoring also requires placement of the electrodes on the torso. In each of the systems for alternative electrode placement, useful ECG data is obtained, but the data differs significantly from standard EGC data. Important differences in amplitudes and waveforms occur between standard ECGs and alternative electrode placement ECGs.

Due to tile differences between data obtained from standard ECGs and alternative electrode placement ECGs, a complication in ECG analysis arises when all ECG test results, regardless of the type of electrode placement, are stored in the same hospital storage system. The same patient may have ECG data stored on the hospital system for a standard ECG and an ECG obtained during a stress test. If no explanation is given for the differences in the data, cardiologists and hospital technicians may be confused when both sets of ECG data are viewed together.

SUMMARY OF THE INVENTION

Accordingly, the invention provides a method and apparatus for analyzing twelve-lead electrocardiograms (ECGs) and for identifying the angles between all the lead vectors. This information allows recognition of the placement of electrodes (either the unintended misplacement or the intentional choice of alternative placements), without the requirement for additional placement of other devices on the patient such as belts, pads, vests, harnesses, electrode strips, or non-standard additional electrodes, and without the need for additional electronics such as impedance current injectors, impedance measurement circuits, sonic or magnetic digitizers, and/or digital cameras.

For the method of the invention, ten seconds of ECG data from eight leads is gathered. Data from two of the frontal leads and all six of the horizontal leads is gathered. A representative heartbeat is located in each channel of data, and sources of interference are filtered from the data. A covariance matrix is then formed with the eight channels of remaining data.

The invention then employs matrix mathematics, referred to as the Karhunen-Loeve transform (KLT), singular value decomposition, principal components analysis, or principal forces analysis, to discover a set of basis vectors or eigenvectors that organize the variability of data in a multidimensional space along new directions, orthogonal to each other and ranked in order of significance. For each eigenvector, a corresponding eigenvalue is calculated. In addition, eigenvalue coefficients are calculated which correspond to the portion of each eigenvector that is necessary to reconstruct each original lead vector. This technique has been used in the prior art to reduce the redundancy of multi-dimensional data, to compress and transmit ECG data, to organize features for ECG waveform classification, and to reduce noise sources in ECG. However, none of the disclosed prior uses of KLT, SVD, PCA, PFA, or like methods allow the identification of electrode placement.

From the eigenvector solution of the covariance matrix, the angles between the eigenvectors and the original vectors are determined. The eigenvalue coefficients and the angles between the eigenvectors and the original vectors are related by a cosine relationship. The angles calculated for each particular ECG test can be compared to a reference set of angles to determine whether the electrodes are placed in the standard or resting ECG electrode placement, an alternative electrode placement, or an incorrect electrode placement.

The invention further includes an ECG machine capable of alerting an ECG technician of non-standard or incorrect electrode placement. The ECG machine is capable of instructing the ECG technician as to how far and in what direction the electrodes are out of place. The ECG machine is also capable of labeling the ECG test data with information regarding the particular type of electrode placement used during the ECG test, including standard electrode placement and various alternative electrode placements.

The invention still further includes a software program capable of analyzing ECG test data. The software program is capable of analyzing ECG data to determine what type of electrode placement was used during the test. The software program can then label the ECG test data to inform cardiologists that standard electrode placement was used or an alternative electrode placement was used.

It is an advantage of the invention to provide a method of evaluating lead placement in an ECG.

It is another advantage of the invention to eliminate the need to manually measure the positions of the electrodes on the patient.

It is still another advantage of the invention to provide a method of evaluating lead placement for stored ECGs, i.e., ECGs that have previously been acquired and copied into patient information storage and retrieval systems.

It is still another advantage of the invention to provide a method of evaluating lead placement in an ECG, which method does not require prior knowledge about how the electrodes were originally placed on the patient.

Various other features and advantages of the invention are set forth in the following drawings, detailed description and claims.

BRIEF DESCRIPTION OF THE DRAWINGS

FIGS. 7 through 12 are lead angle presentations produced by the method of this invention from actual 12 lead ECGs recorded in a controlled environment where electrode placements were systematically adjusted.

FIG. 9 illustrates a lead angle presentation for an electrode placement error in which lead v5 is placed 2 cm too low.

DESCRIPTION OF THE PREFERRED EMBODIMENT

The method will be described in the context of twelve-lead electrocardiograms. It is understood that the essence of the invention is applicable to any signal-processing environment where a redundancy of data can be used to infer relationships between the sources of the data regarding directions and/or angles. The scope of the invention is not limited to one heartbeat or ten seconds of ECG. The scope of the invention is not limited to eight or twelve leads or channels, but the example of a ten second, twelve-lead ECG is very useful and common and will be used herein for the purpose of describing the invention.

Figure 1:
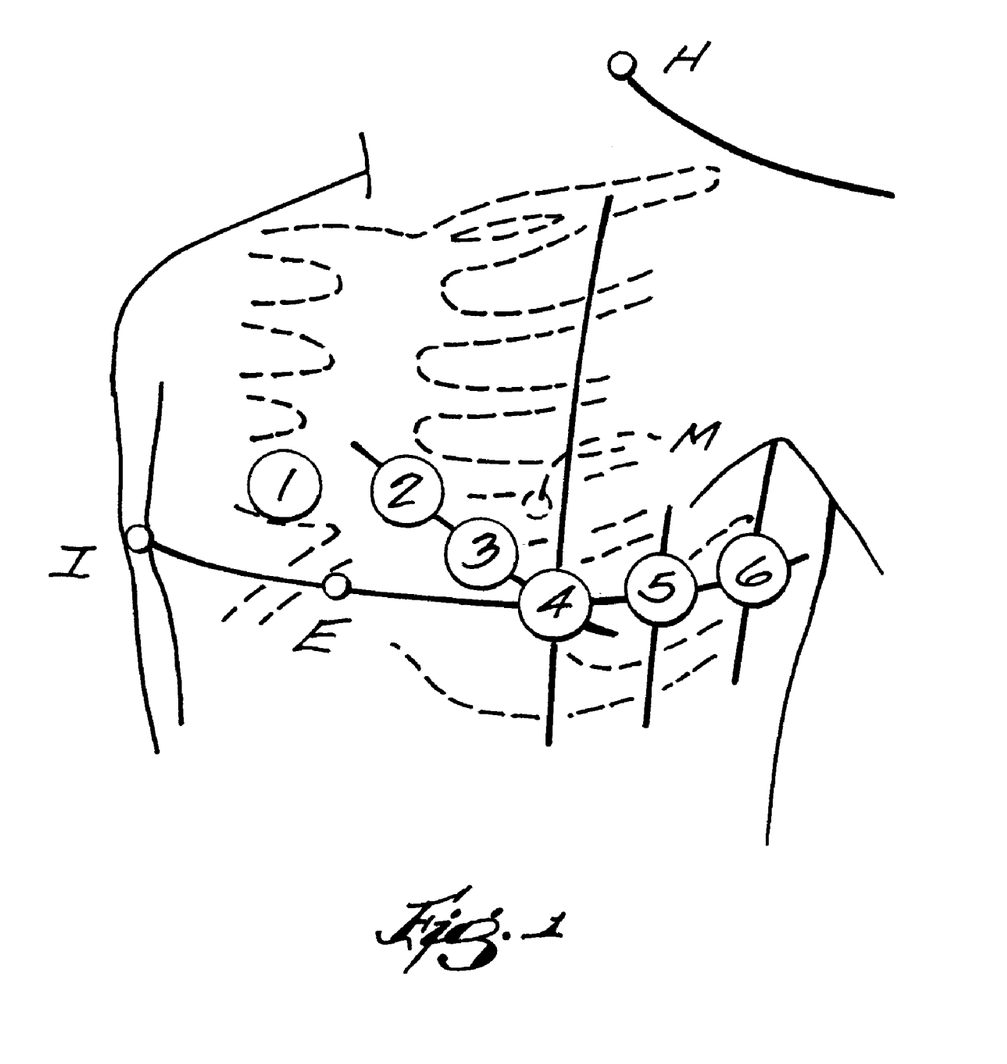
FIG. 1 illustrates the electrode placement for a standard or resting twelve-lead ECG.
Figure 2:
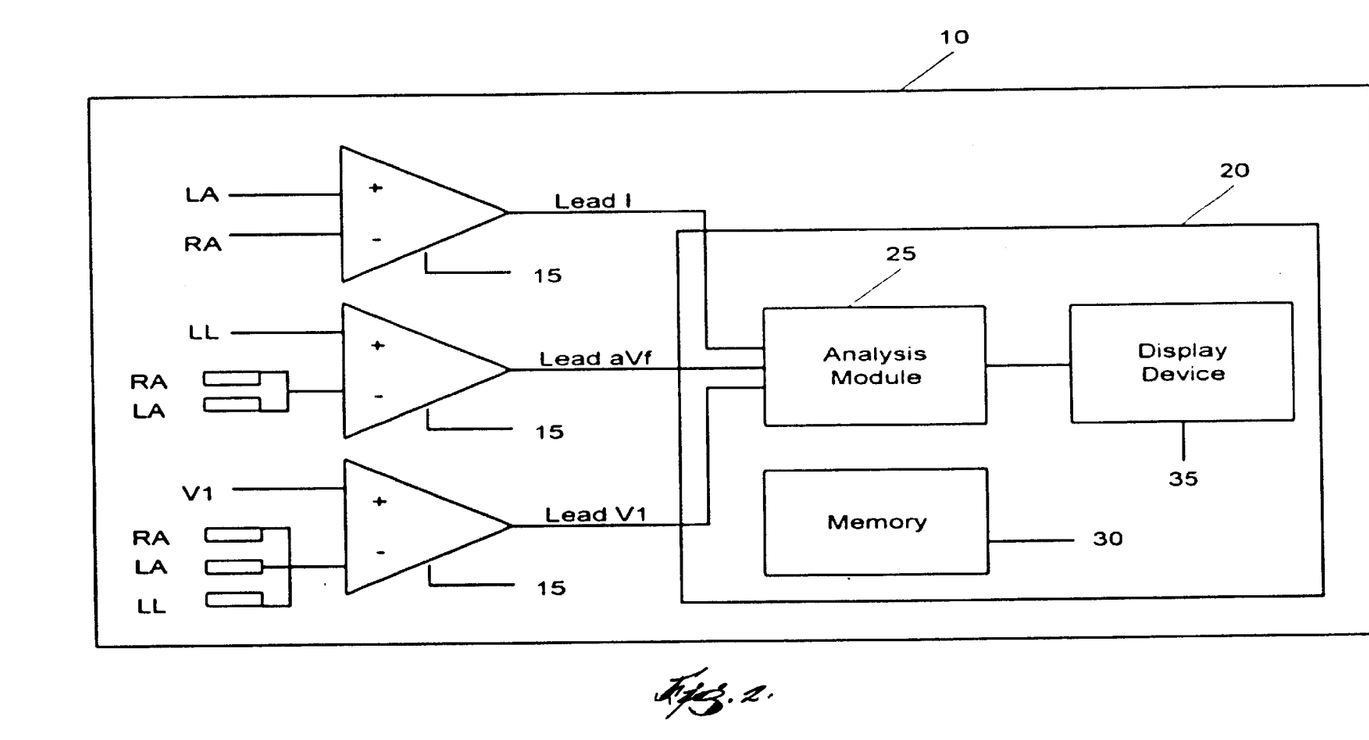
FIG. 2 illustrates the amplifier connections for three types of leads: bipolar (I, II, III), augmented (aVr, aVl, aVf), and unipolar (v1, v2, v3, v4, v5, v6).

FIG. 2 illustrates an ECG machine 10 embodying the invention. While the invention is described in the context of an ECG machine, other devices embodying the invention include data storage and retrieval devices used for long term storage of patient data. In such devices, the ECG data is originally acquired or input from an ECG machine or other patient monitoring device (e.g. stress testing machine, Holter monitor, bedside monitor, etc.), and is stored in memory (not shown) for later (even long term) retrieval and analysis. The ECG machine 10 includes lead wires LA, RA, LL, RL and v1–v6 (only a few of which are shown in FIG. 2). For a standard ECG, ten electrodes are attached to a patient's body. One electrode is attached to each of the patient's four limbs at the wrists and ankles. These electrodes are referred to as left arm (LA), right arm (RA), left leg (LL), and right leg (RL). As shown in FIG. 1, six electrodes are attached in standard positions on the chest around the heart. As is commonly known in the art, the ten electrodes are connected via the respective lead wires and several resistor networks (not shown) to enough amplifiers 15 (only a few of which are shown in FIG. 2) to record twelve separate ECG signals or twelve leads.

The leads are split into two groups: the frontal plane and the horizontal plane. If a straight line were drawn from the heart to each wrist and each ankle, the four lines would lie in the frontal plane. Similarly, if a straight line were drawn from the heart to each of the six electrodes placed on the patient's chest, the six lines would generally lie in the horizontal plane. The leads in the frontal plane are referred to as the frontal leads, the limb leads, the Einthoven leads, or the bipolar leads, and include leads I, II, III, aVr, aVl, and aVf. The leads in the horizontal plane are referred to as the horizontal leads, the precordial leads, the chest leads, or the unipolar leads, and include leads v1, v2, v3, v4, v5, and v6.

The frontal leads are obtained with various permutations of the LA, RA, and LL electrodes, with the RL electrode serving as an electrical ground. As shown in FIG. 2, bipolar leads are comprised of the potential between two electrodes: lead I corresponds to the potential between LA and RA, lead II corresponds to the potential between LL and RA, and lead III corresponds to the potential between LL and LA. As shown in FIG. 2, augmented leads are comprised of the potential between one electrode and a reference input, the reference input being the average of two electrodes. For example, lead aVf is the signal between LL and a reference input, where the reference input is the average of the potentials at electrodes RA and LA.

As shown in FIG. 2, the horizontal leads are obtained with various permutations of the six electrodes attached to the patient's chest, in addition to the four limb electrodes. Each of the six horizontal leads is comprised of the signal between the potential at the particular electrode placed on the patient's chest and the potential at Wilson's central terminal. Wilson's central terminal refers to the average potential between the RA, LA, and LL electrodes. For example, lead v1 is the signal between electrode v1 and Wilson's central terminal.

The ECG machine 10 also includes an ECG control 20 connected to the amplifiers 15. The ECG control 20 receives the ECG data from the amplifiers 15, analyzes the ECG data and stores the ECG for later retrieval. The ECG control 20 includes an analysis module 25 for analyzing the ECG data. As will be appreciated by those of skill in the art, the analysis module 25 can effect analysis of the ECG data using electronic hardware, or a combination of electronic hardware and software.

The ECG control includes a summary storage device 30, and a display device 35 connected to the analysis module 25. The display device 35 may be a printer or monitor, and any number of display devices may be connected to or controlled by the analysis module 25. Moreover, other external connections (not shown) or other internal devices (also not shown) may be included in the ECG machine to effect long term storage and retrieval of ECG data and other patient data.

Generally, twelve channels of ECG data are acquired by the ECG machine 10 and stored in the memory storage device 30. Most of the data acquired from the six frontal leads is repetitive data. It is well known in the art that the six frontal plane leads are easily related to each other by Einthoven's triangle. Kirchhoff's voltage law can be used with lead vectors I, II, and III, forming a triangle in the frontal plane, known as Einthoven's triangle. If any two vectors are known, the third vector can be calculated, because the sum of the three vectors must equal zero. Only two leads of the three leads contain independent data. Moreover, leads aVr, aVl, and aVf are just permutations of leads I, II, and III, so if any two frontal leads are known, the other four frontal leads can be calculated.

Figure 13:
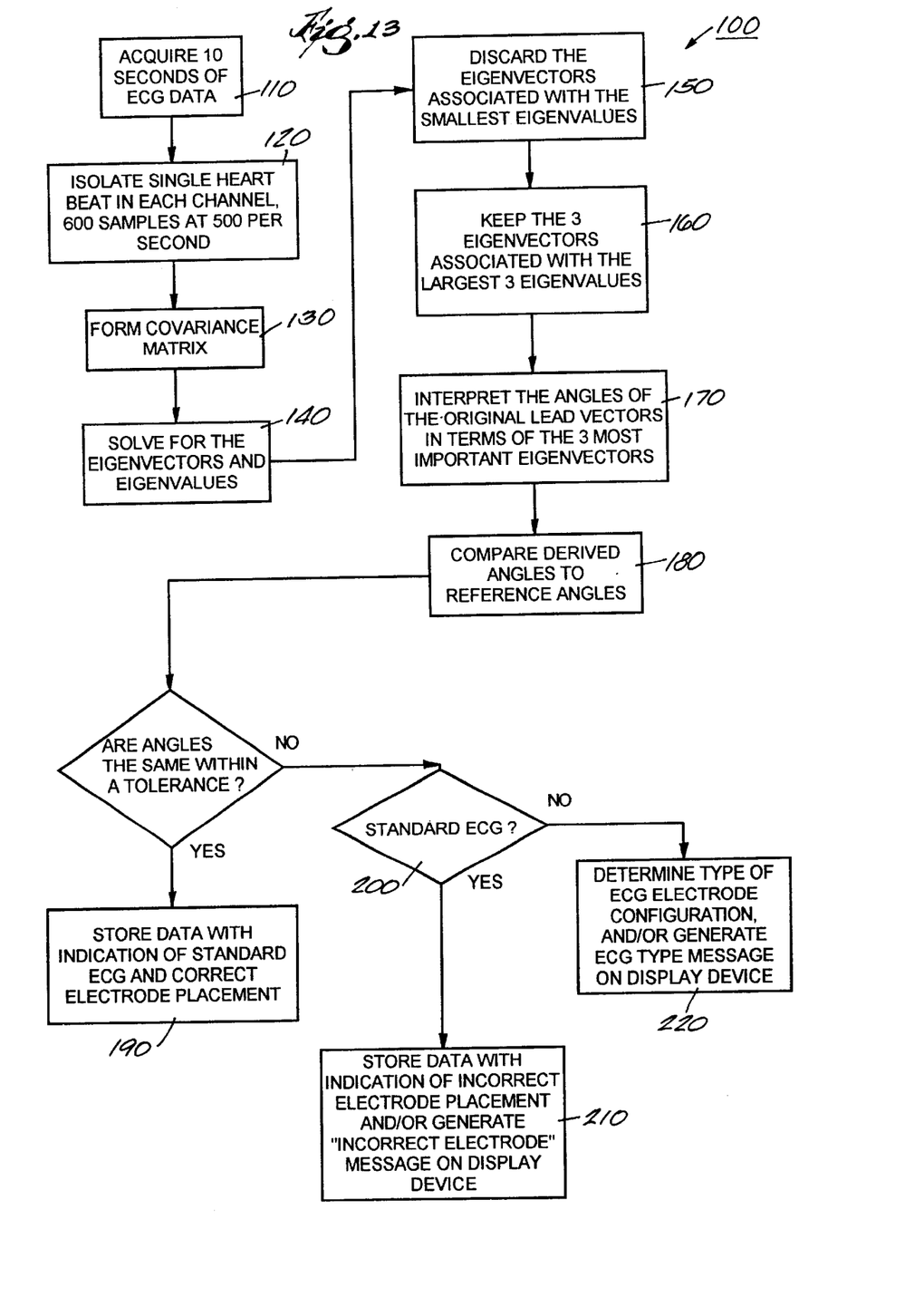
FIG. 13 is a flow chart of the mathematical process for the method of the invention.

As shown in the block diagram of FIG. 13, the method of the invention begins with the acquisition of the lead data. Due to the repetition of the data, only the data from two frontal leads is gathered. In the preferred embodiment, only the data from leads I and II is gathered. If only the data from leads I and II is gathered, the data for the remaining four frontal leads is calculated using the following equations:

$$III=II-I$$

$$aVr=-(I+II)/2$$

$$aVl=(I-III)/2$$

$$aVf=-(II+III)/2$$

Figure 3:
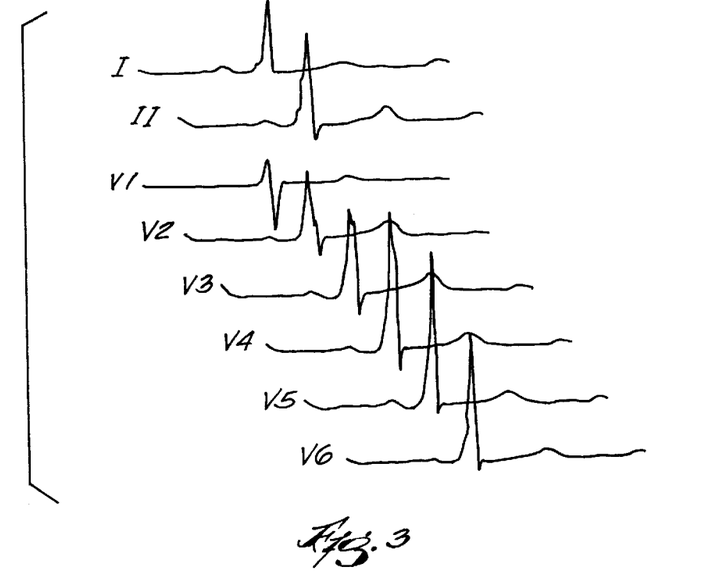
FIG. 3 is a graphical illustration of eight original lead vectors (I, II, v1, v2, v3, v4, v5, v6) of a single heartbeat.

In addition to the two frontal leads, data is gathered from each of the six horizontal leads. Only ten seconds of data from each of the eight leads is necessary to practice the method of the invention. Ten seconds of eight channels of ECG is gathered at 500 samples per second. The data from each of the original eight leads is shown in FIG. 3. From this data, a representative heartbeat is located or derived in each channel by methods known in the art. Sources of interference, such as power line frequencies, respiration, muscle tremor, or baseline drift, are then removed. The remaining signal represents only the electrical activity of the heart according to the dipole model. This signal is dominated by an equivalent instantaneous electrical vector in three dimensions located at a point source within the heart. It is assumed that the recorded voltages on the body surface are principally projections in different directions of that instantaneous electrical vector.

Once the data is acquired and filtered, the analysis module 25 forms a covariance matrix of the ECG data. The method includes removal of the mean value from each of eight lead vectors consisting of, for example, 600 samples each. Each vector is multiplied by each other vector, sample by sample, and the products summed to obtain the dot product solution. The dot product solution is referred to as the covariance. ECG leads that are very similar in shape will have high covariances.

The analysis module 25 then calculates the eigenvector solution to the covariance matrix using one of the following generally equivalent mathematical methods: Karhunen-Loeve transform (KLT), singular value decomposition, principal forces analysis, or principal components analysis. The method referred to for purposes of this description is the Karhunen-Loeve transform or KLT.

The KLT is most easily understood in the context of three-dimensional data, such as data acquired using the Frank lead system. FIG. 1 illustrates the Frank lead system, which in addition to the standard ten ECG electrodes, includes four additional electrodes (H,I,E,M). The Frank lead system is used to acquire data that represents the heart activity in only three vectors. Basically, the KLT is applied to the data to analyze the variability of the data in the x, y, z coordinate system and determine a new u, v, w coordinate system. More specifically, KLT is implemented by the analysis module 25 to determine the direction in which there is the most variation in the data. The direction of most variability in the data becomes the u coordinate. The direction with the second most variability becomes the v coordinate, with the v coordinate being perpendicular to the u coordinate. The direction with the third most variability becomes the w coordinate, with the iv coordinate being perpendicular to the plane defined by the u and v coordinates. From the first three directions of variation, a new three-dimensional coordinate system is established that corresponds to each particular set of data. The first three eigenvectors correspond to the first three directions of most variability represented by the u, v, and w coordinates. Although difficult to visualize, each additional direction of variability is also determined by the KLT. These additional dimensions may represent variations in the patient's tissue, such as whether the electrode is placed over rib bones or over intercostal space.

Figure 4:
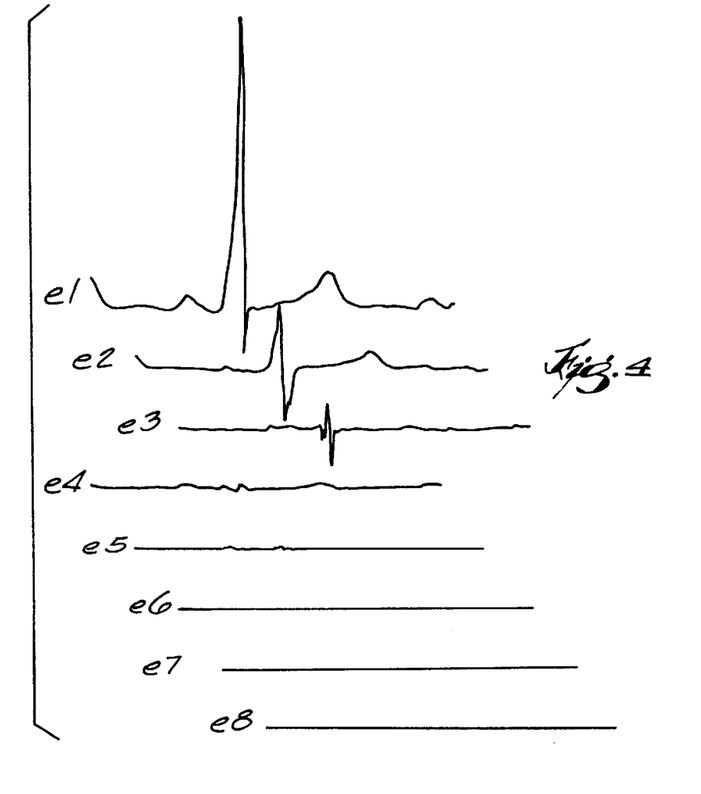
FIG. 4 is a graphical illustration of the projection of the data in FIG. 3 onto eight eigenvectors (e1, e2, e3, e4, e5, e6, e7, e8) demonstrating the limited signal content beyond the first three vectors.

Since most data can be represented with three dimensions, the first three directions of variability, and thus, the first three eigenvectors are the most significant. The eigenvector solution for the original data from FIG. 3 is shown in FIG. 4. For clarification purposes, the first eigenvector (e1) does not correspond to the data from lead I, rather the first eigenvector (e1) corresponds to the direction of most variability of the data from all eight leads. As shown in FIG. 4, the first three eigenvectors (e1, e2 and e3) contain most of the relevant data, since the fourth through eighth eigenvectors (e4, e5, e6, e7 and e8) have limited signal content. Moreover, it is clear from FIG. 4 that most of the heart's activity is along a single direction represented by the first eigenvector.

Eigenvalues for each eigenvector are then determined by the analysis module 25 from the position of each data point along the eigenvector. Each data point is given a value corresponding to the variation of the data point from the eigenvector. The mean of the values corresponding to each data point is found. The standard deviation from the mean is considered the eigenvalue for that particular eigenvector. The eigenvalues for the first three eigenvectors will be the largest, since the first three eigenvectors represent the directions along which the data varies the most.

Figure 5:
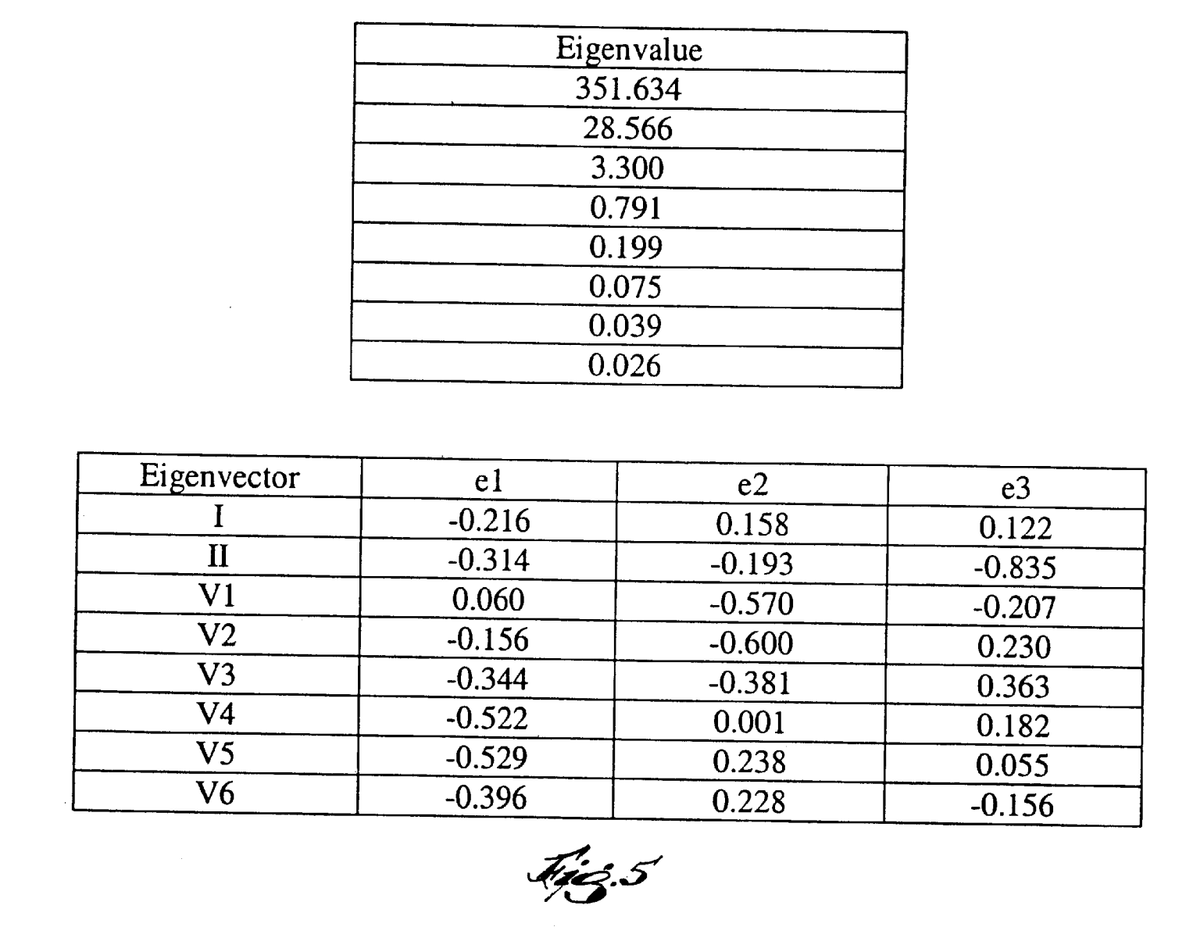
FIG. 5 includes two tables. The first table shows the total eigenvalue for each of the eigenvectors in FIG. 4. The second table shows the coefficients that correspond to each eigenvector and each original lead vector.
Figure 6:
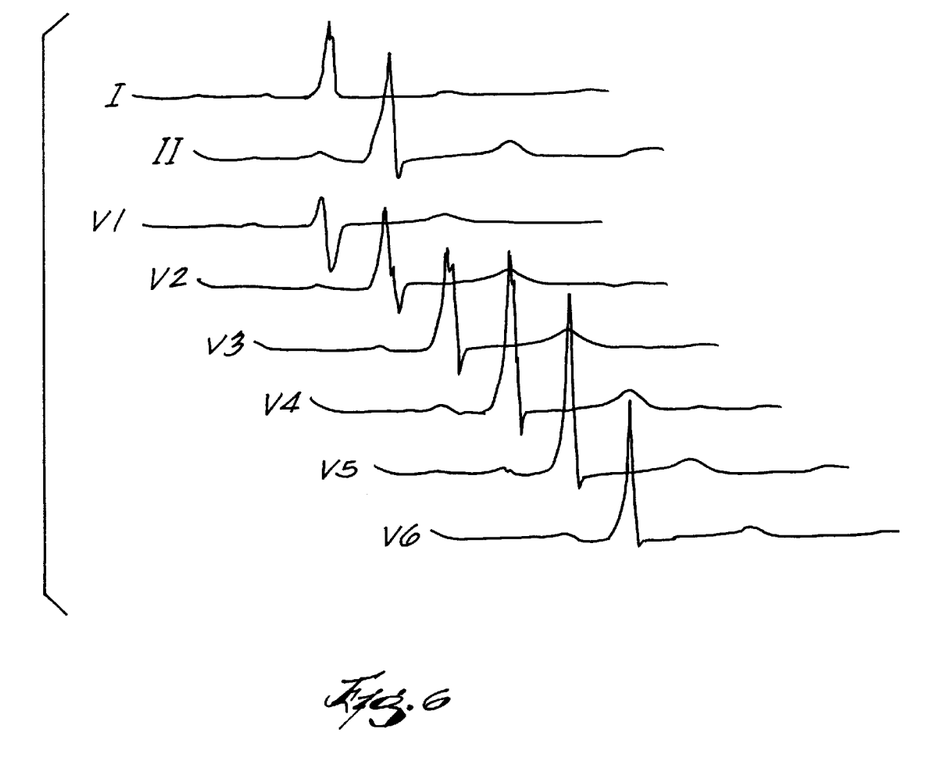
FIG. 6 is a graphical illustration of the original lead vectors reconstructed from the eigenvector solution.

For the method of the invention, all but the three largest eigenvalues and their corresponding eigenvectors are discarded. As shown in FIG. 5, tables for all the eigenvalues and the most important three eigenvectors are constructed. The first table of eigenvalues in FIG. 5 corresponds to the total eigenvalues for each of the eight eigenvectors. The second table in FIG. 5 consists of the coefficients of each eigenvector necessary to reconstruct the original lead data. For example, original lead I is approximately represented by about 20% of eigenvector e1, 15% of eigenvector e2, and 12% of eigenvector e3. As shown in FIG. 6, the eigenvalues and their corresponding eigenvectors can be used to accurately reconstruct the original data.

More importantly than reconstructing the original data, the coefficients in the second table in FIG. 5 can be used to determine the angles between each of the original lead vectors and the eigenvectors. The eigenvalue coefficients in the second table can be interpreted as cosines of the angles between each original lead vector and the eigenvector. For example, the eigenvalue coefficient corresponding to eigenvector e1 and lead v4 is –0.522. The cosine of 60 degrees is 0.5. Thus, the angle between eigenvector e1 and lead v4 is about 60 degrees. Similarly, the eigenvalue coefficient corresponding to eigenvector e2 and lead v1 is –0.570, so the angle between eigenvector e2 and lead v1 is also about 60 degrees. Since the cosine of 90 degrees is zero, as the coefficients approach zero, the angle between the eigenvector and the original lead approaches 90 degrees. For example, the eigenvector coefficient corresponding to eigenvector e2 and v4 is 0.001, thus the angle between eigenvector e2 and original lead v4 is almost 90 degrees.

A reference eigenvector solution including a set of reference angles representative of a typical standard or resting ECG is stored in the memory 30 of the ECG machine 10. The angles between the eigenvectors and the original lead vectors for a particular ECG test are determined and then compared to the reference angles. If the angles for the ECG test do not match with the reference angles, the electrode placement is determined by the analysis module 25 to be either non-standard or incorrect. For example, the reference angle between eigenvector e1 and lead v2 may be about 90 degrees. If an ECG test is conducted and the angle between eigenvector e1 and lead v2 is only 30 degrees, electrode v2 is not in the correct position on the patient's chest for standard electrode placement.

Figure 7:
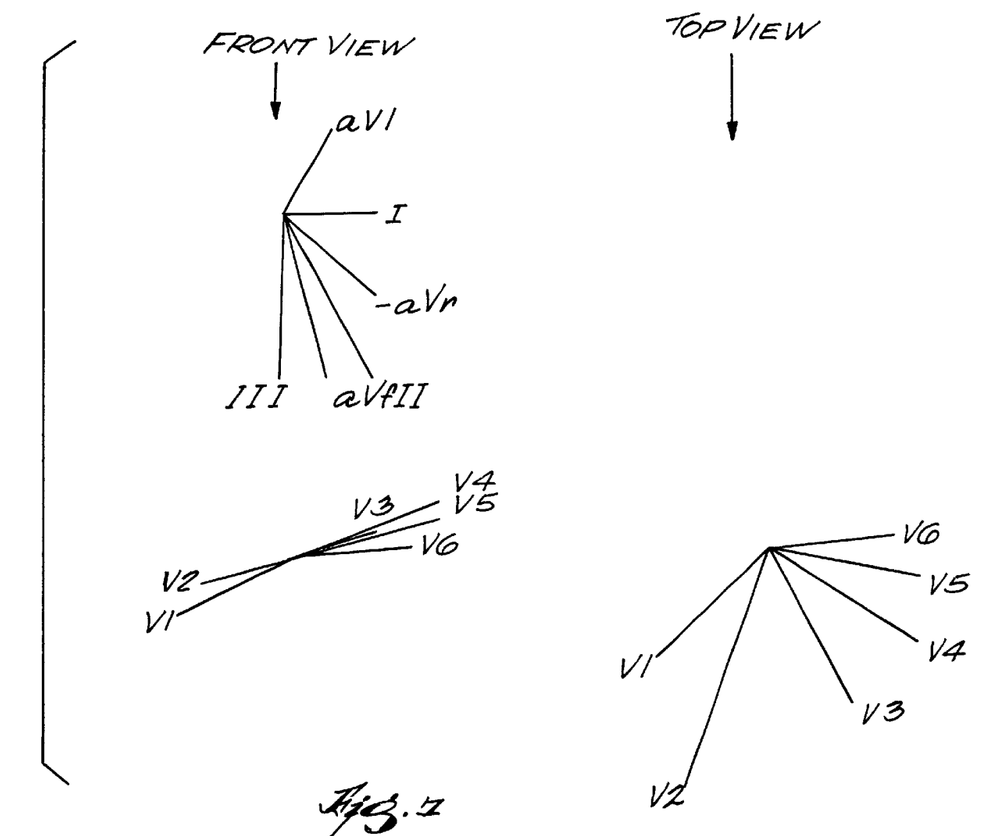
FIG. 7 illustrates the lead angle presentation for standard electrode placement.
Figure 8:
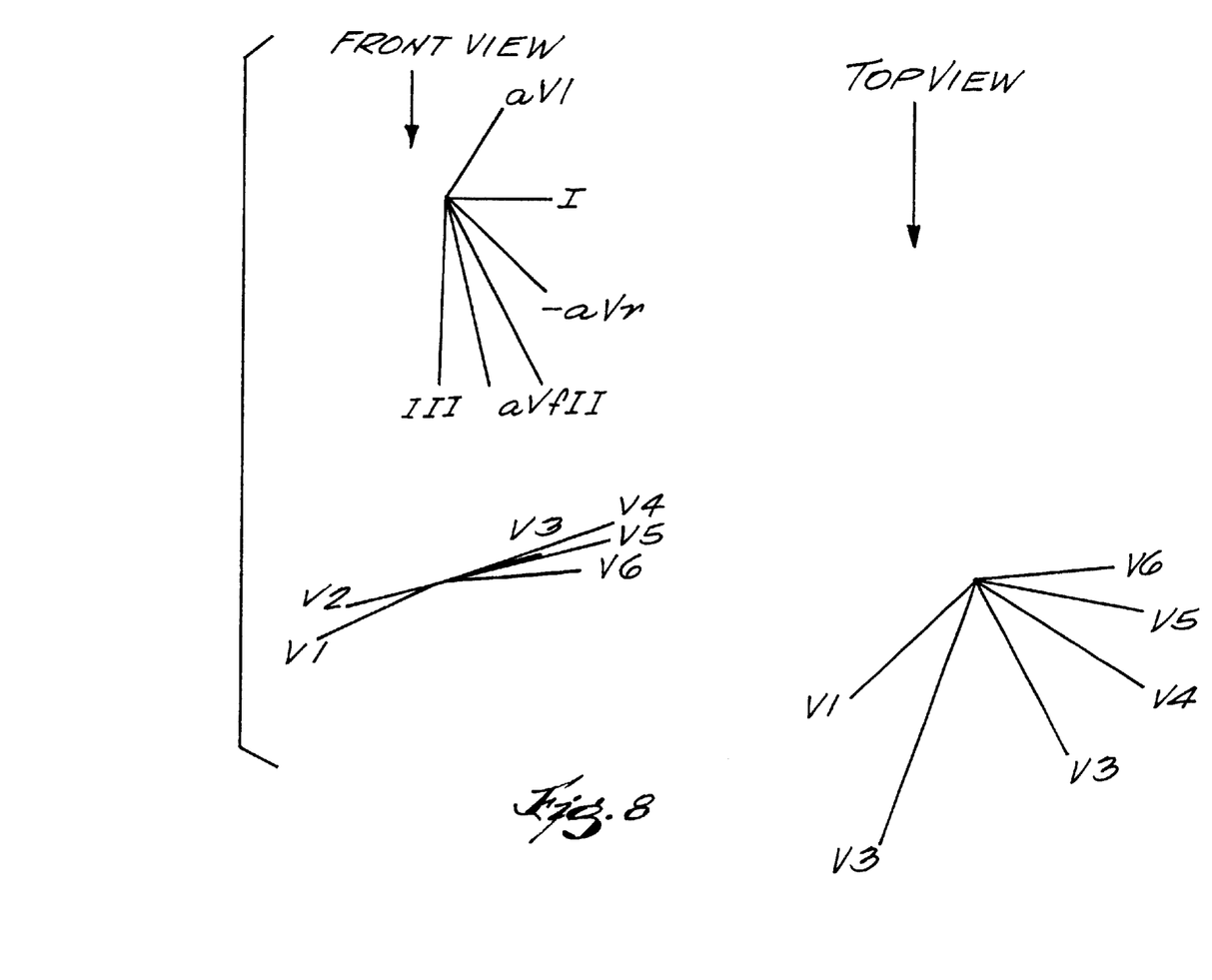
FIG. 8 illustrates a lead angle presentation for an electrode placement error in which leads v1 and v2 have been reversed.

FIG. 7 illustrates the lead angle presentation for standard electrode placement. The frontal plane leads are only shown from the front, since these leads are defined to lie exactly in the frontal plane. The lead angle presentation in FIG. 7 serves as the reference for standard electrode placement for comparison with the lead angle presentations in FIGS. 8–12. A comparison between the reference angles in FIG. 7 and the lead angles in FIG. 8 shows that leads v1 and v2 have been reversed. A comparison between FIG. 7 and FIG. 9 shows that lead v5 is placed 2 cm too low.

Figure 10:
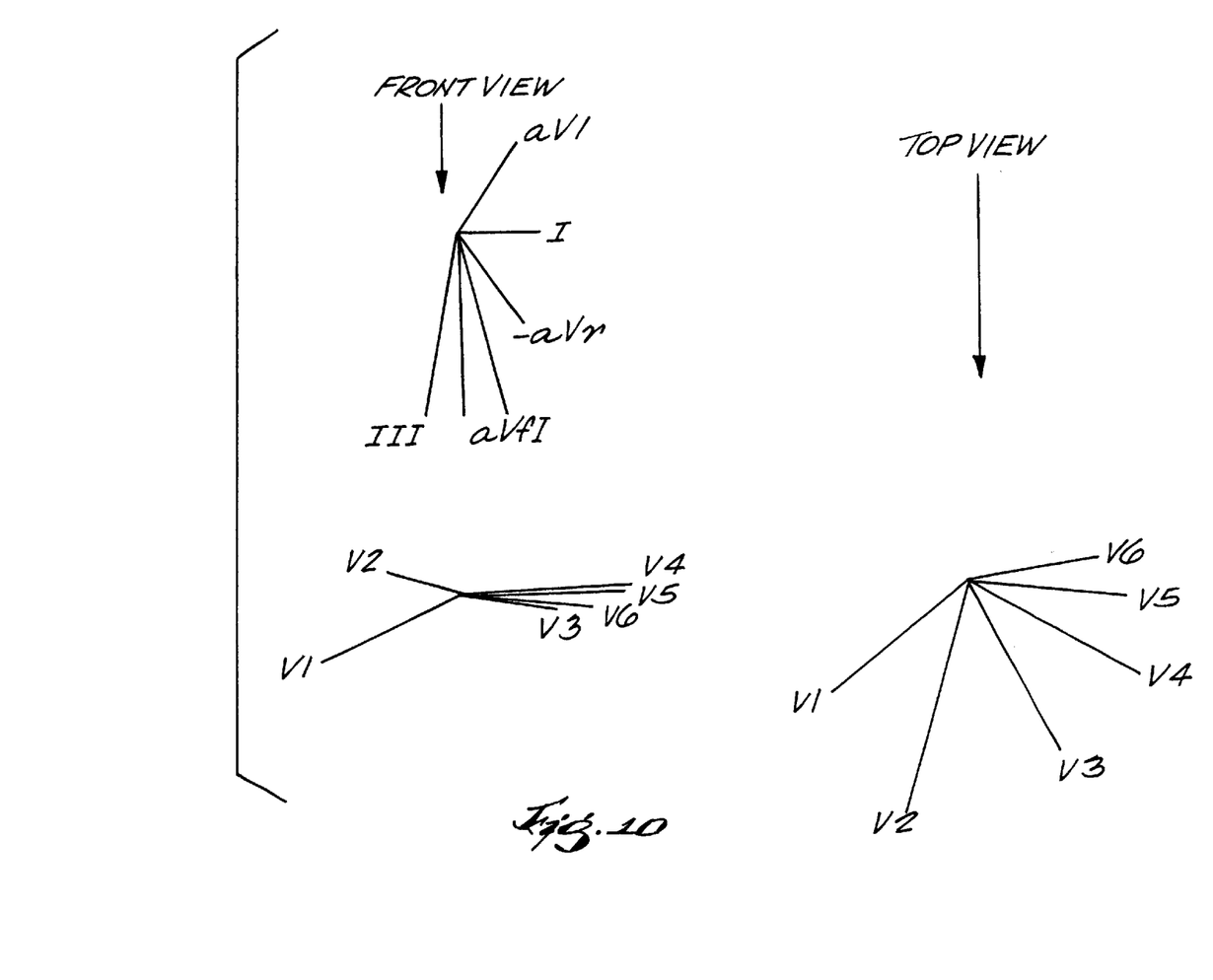
FIG. 10 illustrates the lead angle presentation for Mason-Likar electrode placement.
Figure 11:
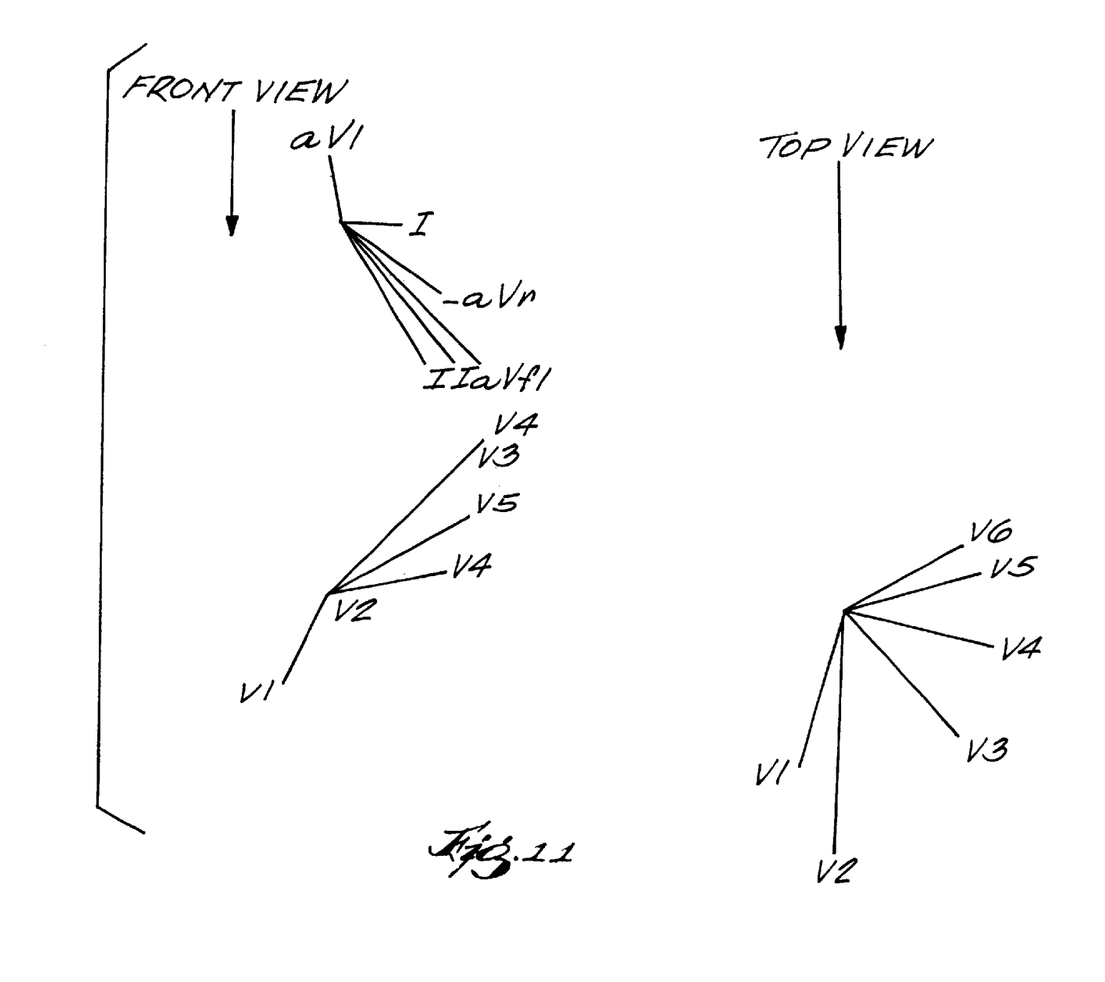
FIG. 11 illustrates a lead angle presentation for an alternative electrode placement, similar to Mason-Likar electrode placement.
Figure 12:
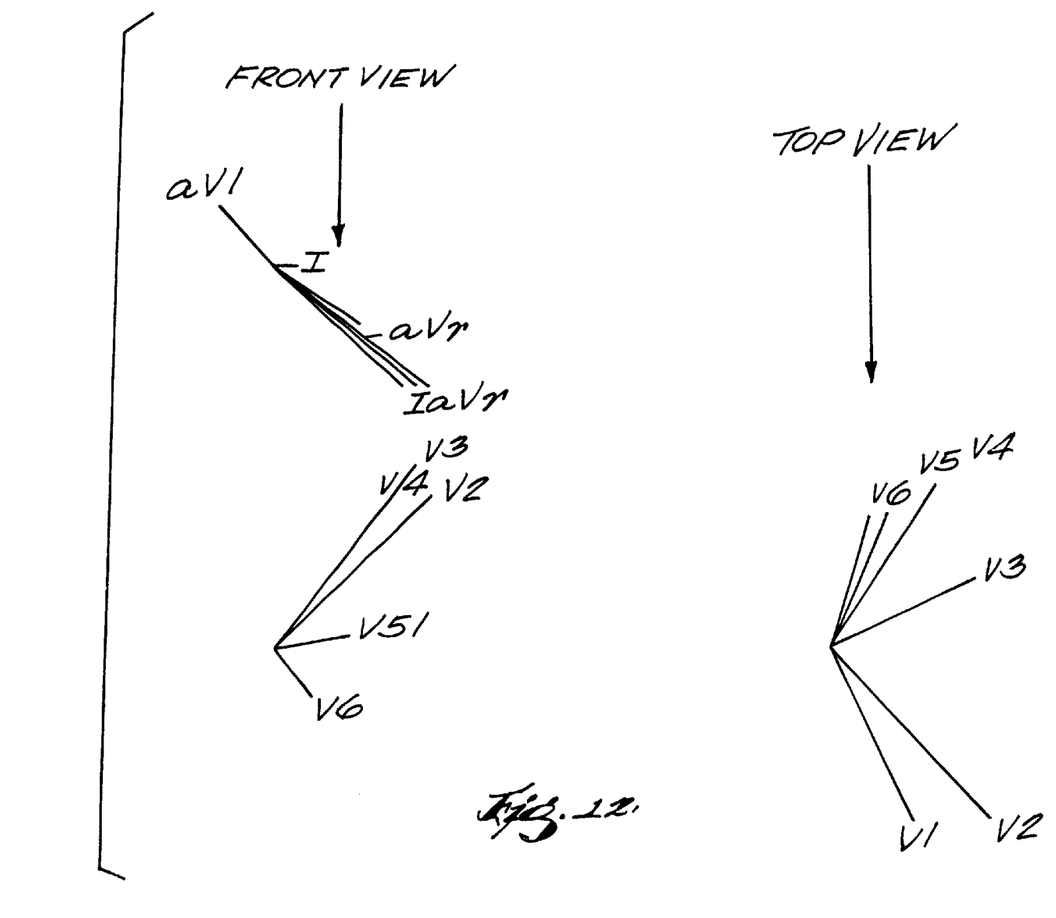
FIG. 12 illustrates a lead angle presentation for an alternative electrode placement that is distorted from the standard lead angle presentation.

FIGS. 10, 11, and 12 depict lead angle presentations for alternative electrode placement schemes. FIG. 10 shows the lead angle presentation for Mason-Likar electrode placement. For Mason-Likar electrode placement, the limb electrodes are placed at the outside tips of the shoulders and at the hips. The lead angle presentation for Mason-Likar electrode placement compares favorably to the standard lead angle presentation in FIG. 7. FIG. 11 shows an alternative to Mason-Likar electrode placement, in which the limb electrodes are placed at the middle of the collarbones and at the hips. The leads are presented in a more vertical alignment for this alternative electrode placement. Since the arm electrodes are placed closer together than for standard electrode placement, lead I becomes much shorter. FIG. 12 shows another alternative to Mason-Likar electrode placement, in which the limb electrodes are placed just to the left and right of the sternum and at the bottom of the rib cage. This electrode placement presents an extreme distortion to the standard lead angle presentation in FIG. 7.

The results obtained from the above-described mathematical process can be used during an ECG test in two ways: (1) to alert an ECG technician to reversed or incorrectly positioned electrodes, and (2) to alert an ECG technician to non-standard electrode placement. In a situation in such as LA/RA reversal, the analysis module 25 alerts the ECG technician via the display device 35 that the leads are reversed. In a situation in which one of the horizontal leads is placed incorrectly on the chest, the anlaysis module 25 alerts the ECG technician to the incorrect lead placement and instructs the technician how far and in what direction to reposition the electrode. In the case of non-standard electrode placement, the ECG machine 10 simply defines the non-standard placement, e.g. Holter or stress and provides an indication on the display, and in the memory of the non-standard electrode placement.

FIG. 13 illustrates a flowchart detailing the method of the invention. The method includes the acts of acquiring ten seconds of ECG information 110; isolating a single heartbeat in each channel of the ECG data 120; forming a covariance matrix of the ECG data 130; solving for the eigenvectors and eigenvalues of the covariance matrix 140; discarding the eigenvectors associated with the smallest eigenvalues 150; keeping the three eigenvectors associated with the largest three eigenvalues 160; interpreting the angles of the original lead vectors in terms of the three most important eigenvectors 170; and comparing the derived angles to reference angles 180. After the comparison, if the angles are the same within a tolerance, then the ECG data is stored in a memory with an indication that the data is from a standard ECG and that the correct electrode placement was used 190. If the angles are not within a tolerance, then the method determines whether the ECG data is from a standard ECG 200. If the ECG data is from a standard ECG, then the ECG data is stored in the memory with an indication that the electrodes were placed incorrectly during acquisition of the ECG data 210. If the ECG data is determined not to be standard ECG data, then the ECG data is further analyzed to determine the type of ECG electrode configuration 220. The information relating to the type of ECG configuration or the incorrect electrode placement may either be displayed on the display device immediately upon acquiring the ECG data, or may be stored as a message to be generated later upon production of the ECG report.

The results obtained from the above-described mathematical process are useful in an ECG machine or in a software package for conducting ECG analysis to determine and record with the ECG data what type of electrode placement scheme is being used or was used with the ECG test, or whether the electrodes were placed in the correct position on the body, or whether leads were accidently switched during the test.

It should be understood that the invention is not limited in its application to the details of the construction and the arrangements of the components set forth in the description or illustration in the drawings. The invention is capable of other embodiments and of being practiced or being carried out in various ways. Also, it is to be understood that the phraseology and terminology used herein is for the purpose of description and should not be regarded as limiting.

What is claimed is:

1. A method to identify electrode placement in a system for acquiring a patient physiological signal through at least three electrodes applied to the patient, each electrode defining an electrical vector relative to a reference, the method comprising:

acquiring the physiological signal; and analyzing the physiological signal to determine whether the electrodes are incorrectly positioned or are positioned in a non-standard configuration.

2. The method of claim 1 wherein the system includes a display device, and wherein the method further comprises the act of generating a message on the display device indicating whether the electrodes are incorrectly positioned or are positioned in a non-standard configuration.

3. The method of claim 1 further comprising the act of comparing the angles between the electrical vectors of the electrodes to a standard to determine whether the electrodes are in the correct position.

4. The method of claim 1 wherein the act of analyzing includes computing the covariance matrix of the physiological signal for the at least three electrodes, computing eigenvectors and eigenvalues of the covariance matrix, and evaluating the eigenvectors associated with the largest eigenvalues to determine the angles between the electrical vectors of the electrodes.

5. The method of claim 4 wherein the eigenvector solution is computed using a one of singular value decomposition (SVD), Karhunen-Loeve transform (KLT), principal components analysis and principle forces analysis.

6. The method of claim 4 wherein the system includes a display device, and wherein the method further comprises the act of generating a message on the display device indicating whether the electrodes are in the correct position.

7. The method of claim 1 and further comprising the act of comparing the angles between the electrical vectors of the electrodes to a standard to determine whether the electrodes are in a non-standard configuration.

8. The method of claim 1 wherein the system includes a display device, and wherein the method further comprises the act of generating a message on the display device indicating the non-standard configuration.

9. The method of claim 1 wherein the physiological signal is an eight channel electrocardiogram.

10. The method of claim 1 wherein the physiological signal is a twelve channel electrocardiogram.

11. The method of claim 1 wherein the physiological signal is a four channel electrocardiogram.

12. The method of claim 1 wherein the physiological signal is 10 seconds of electrocardiogram.

13. The method of claim 1 wherein the physiological signal is representative of the electric cardiac activity of the patient during at least a single heart beat.

14. The method of claim 1 wherein the physiological signal is representative of the electric cardiac activity of the patient during at least a portion of a single heart beat.

15. The method of claim 1 wherein the eigenvector solution is computed using a one of singular value decomposition (SVD), Karhunen-Loeve transform (KLT) and principal forces analysis.

16. A method to identify electrode placement in a system for acquiring a patient physiological signal through at least three electrodes applied to the patient, each electrode defining an electrical vector relative to a reference, the method comprising:

acquiring the physiological signal;

computing a covariance matrix of the physiological signal for the at least three electrodes;

computing eigenvectors and eigenvalues of the covariance matrix; and evaluating the eigenvectors associated with the eigenvalues to determine the angles between the electrical vectors of the electrodes.

17. A device for analyzing physiological patient data originally acquired from a patient via electrodes applied to the patient such that the electrodes define an electrical vector relative to a reference, the device comprising:

an input for receiving the physiological patient data; and an analysis module including software for analyzing the physiological data to determine the angles between the electrical vectors.

18. A device as set forth in claim 17 and further comprising a memory connected to the analysis module to store the physiological patient data.

19. A device as set forth in claim 17 wherein the analysis module computes a covariance matrix of the physiological signal for the at least three electrodes, computes eigenvectors and eigenvalues of the covariance matrix, and evaluates the eigenvectors associated with the largest eigenvalues to determine the angles between the electrical vectors of the electrodes.

20. A device as set forth in claim 17 wherein the analysis module compares the angles between the electrical vectors of the electrodes to a standard to determine whether the electrodes are in a non-standard configuration.

21. A device as set forth in claim 20 and further comprising a display device for displaying an indication of the non-standard electrode configuration.

22. A device as set forth in claim 17 wherein the analysis module compares the angles between the electrical vectors of the electrodes to a standard to determine whether the electrodes are in the correct position.

23. A device as set forth in claim 22 and further comprising a display device for generating a message indicating whether the electrodes are in the correct position.

24. A device for analyzing physiological patient data originally acquired from a patient via electrodes applied to the patient such that the electrodes define an electrical vector relative to a reference, the device comprising:

an input for receiving the physiological patient data; and an analysis module for determining the position of the electrodes with respect to each other, and for comparing the positions of the electrodes to a standard in order to determine whether the electrodes are incorrectly positioned or are positioned in a non-standard configuration.

25. A device as set forth in claim 24 and further comprising a memory connected to the analysis module to store the physiological patient data.

26. A device as set forth in claim 24 wherein the analysis module computes a covariance matrix of the physiological signal for the at least three electrodes, computes eigenvectors and eigenvalues of the covariance matrix, and evaluates the eigenvectors associated with the largest eigenvalues to determine the angles between the electrical vectors of the electrodes.

27. A device as set forth in claim 24 wherein the analysis module compares the angles between the electrical vectors of the electrodes to a standard to determine whether the electrodes are in a non-standard configuration.

28. A device as set forth in claim 27 and further comprising a display device for displaying an indication of the non-standard electrode configuration.

29. A device as set forth in claim 24 wherein the analysis module compares the angles between the electrical vectors of the electrodes to a standard to determine whether the electrodes are in the correct position.

30. A device as set forth in claim 29 and further comprising a display device for generating a message indicating whether the electrodes are in the correct position.

* * * * *